Figure 1:
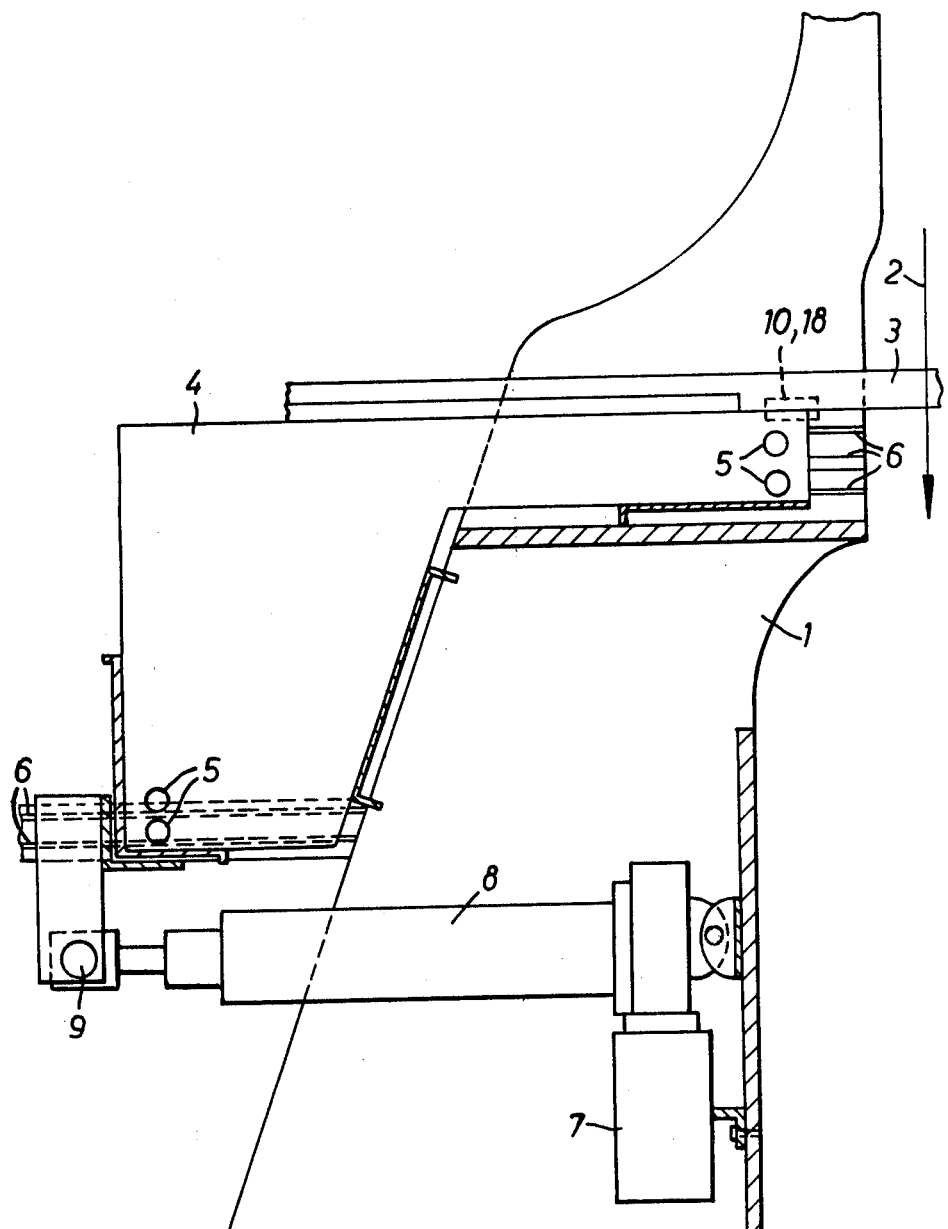

United States Patent [19]

Ingham et al.

[11] 4,097,746
[45] Jun. 27, 1978

[54] DRIVING AND POSITIONING ARRANGEMENT FOR RADIOGRAPHY

[75] Inventors: William Ellis Ingham, Peppard Common, Nr. Henley-on-Thames; Anthony Michael Williams, Iver, both of England

[73] Assignee: EMI Limited, Middlesex, England

[21] Appl. No.: 726,051

[22] Filed: Sep. 23, 1976

[30] Foreign Application Priority Data

Oct. 2, 1975 United Kingdom ............... 40282/75

[51] Int. Cl.² .............................................. G03B 41/16
[52] U.S. Cl. ................................ 250/444; 250/445 T; 250/439 P
[58] Field of Search ................ 250/439, 444, 445 R, 250/445 T, 451, 456

[56] References Cited

U.S. PATENT DOCUMENTS

| | | |
|---|---|---|
| 3,555,276 | 1/1971 | Endesfelder et al. ........ 250/445 R X |
| 3,922,552 | 11/1975 | Ledley ......................... 250/445 T X |
| 3,974,388 | 9/1976 | Distler et al. ..................... 250/445 T |

*Primary Examiner*—Archie R. Borchelt
*Attorney, Agent, or Firm*—Cooper, Dunham, Clark, Griffin & Moran

[57] ABSTRACT

A driving and positioning arrangement for radiography includes a patient support which can be driven, in a direction longitudinally of the patient, through an aperture in a housing which contains the active elements of a computerised tomographic apparatus. A scale member comprises a part which is supported by the housing and a part which is supported by the patient support. Once the patient is correctly positioned for examination, one of the parts of the scale member is moved relative to its respective support so that the two parts can be caused to assume a selected relative position.

3 Claims, 3 Drawing Figures

DRIVING AND POSITIONING ARRANGEMENT FOR RADIOGRAPHY

The present invention relates to a driving and positioning arrangement for radiography, and it relates more especially to such an arrangement for use in computerised axial tomography in which the absorption (or transmission) coefficient, with respect to the radiation employed, is evaluated at each of a plurality of locations distributed over a slice cross-sectionally disposed in a body. One example of such computerized axial tomographic apparatus is described and claimed in U.S. Pat. No. 3778614.

In some circumstances, it is desirable that the body under examination may be movable relative to the tomographic apparatus in a direction longitudinal of the body so as to enable the coefficients relating to locations in other cross-sectional slices to be evaluated. If this facility is to be made available, then it is clearly desirable that the movement of the body may be effected automatically and in controllable manner, and moreover that the position of the body relative to the apparatus be known.

It is an object of this invention to provide a driving and positioning arrangement for radiography having the facility referred to above.

According to the invention there is provided a driving and positioning arrangement for radiography, including a frame member which includes an apertured housing, a carriage, supported by said frame member, the carriage being adapted to support a patient in a generally horizontal position and being movable in a direction longitudinal of the patient's body, and the aperture being such as to accommodate part at least of said body, drive means for moving said carriage, and with it the patient, in said longitudinal direction so as to dispose a predetermined slice of the patient's body in a position, within said housing, in which it can be irradiated with penetrating radiation, and a scale member having first part supported by said frame member and a second part supported by said carriage, said parts being disposed in overlying relationship so as to indicate the disposition of said carriage relative to said frame member, and means for moving at least one of said parts, in said longitudinal direction, relative to its respective supporting member so that said parts can be caused to assume a selected relative position when said selected slice is in said position in which it can be irradiated.

Figure 2:
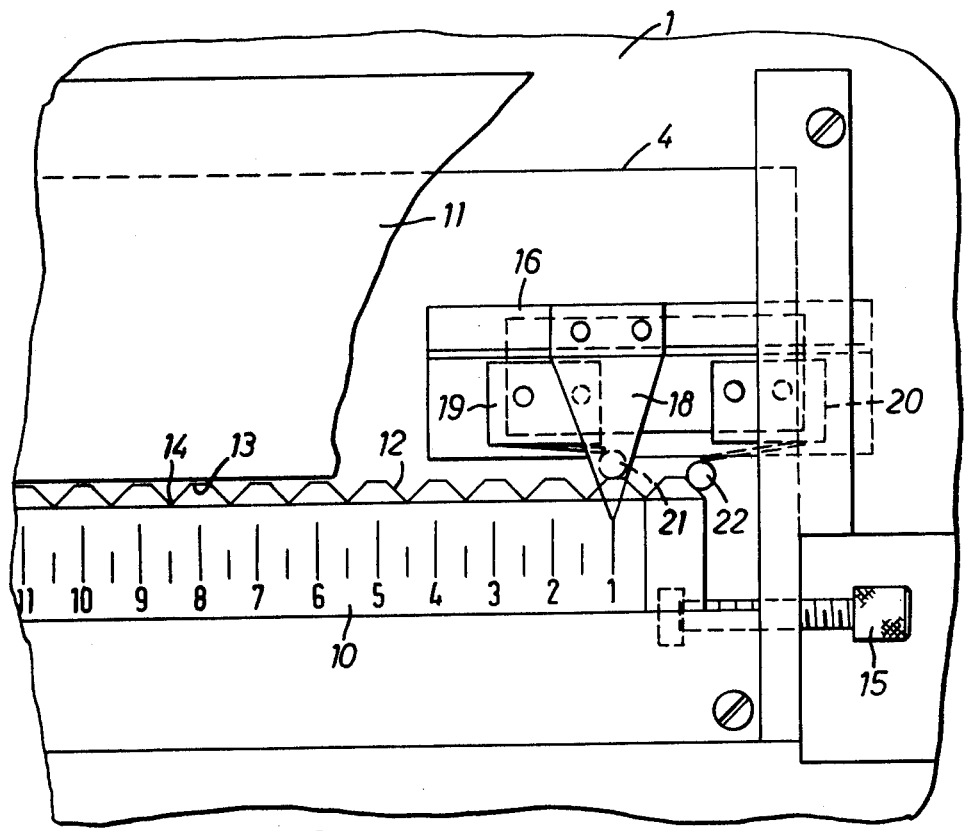
Figure 3:
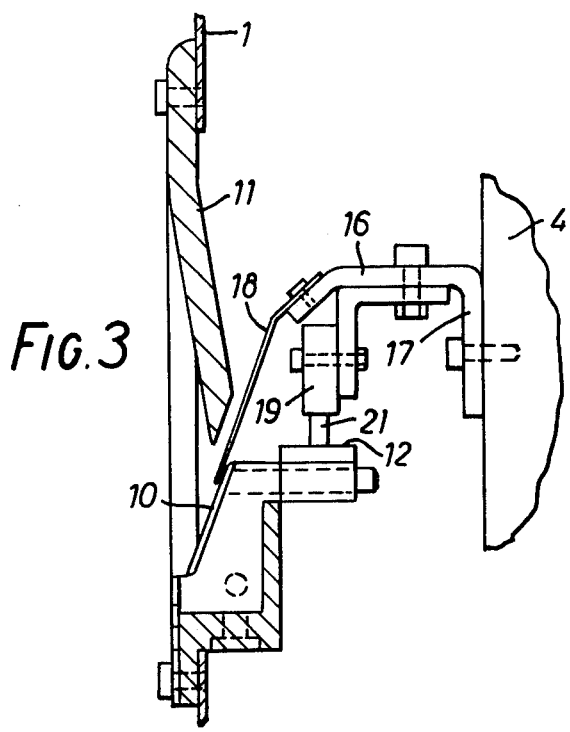

In order that the invention may be clearly understood and readily carried into effect, one embodiment thereof will now be described by way of example only with reference to the accompanying drawings of which:

FIG. 1 shows, in part cross-section, a side elevational view of part of an apparatus suitable for use in accordance with one example of the invention, FIG. 2 shows, in part cross-section, a side elevational view of a scale and rack member for use with the apparatus of FIG. 1, and FIG. 3 shows, in cross-sectional view, a pointer, switch and track follower, member for use with the apparatus of FIGS. 1 and 2.

Referring to FIG. 1, the apparatus comprises a main frame 1 which supports a radiation source, a detector array and a scanning gantry for the source and detector array, none of the components so supported being shown in the drawing because they are not relevant to the understanding of the present invention. It is sufficient to say that the part of a body which is to be examined by the apparatus is positioned so as to be intersected by the arrow 2, which corresponds to the centre line of a plane, perpendicular to the plane of the paper, in which radiation is projected from the source to the detector array.

The body (not shown) is supported on a bed 3 which, in turn, is supported upon a bed carriage 4. The bed carriage 4 is slidably movable relative to the frame 1 by means of rollers such as 5 on the carriage which run on rails such as 6 on the frame 1. The bed 3 is also slidably movable with respect to the carriage 4, for the purpose of facilitating the ingress of a body to the machine. However the sliding movement between the bed 3 and carriage 4 is only operative as between two end stops, "fully out" and "fully in". At all material times during the examination, the bed 3 is locked in its "fully in" position relative to the carriage 4, so this movement will not be further considered.

The movement of the bed 3 relative to frame 1, once the patient is installed in the apparatus, is effected by movement of the carriage 4. This is effected by means of an electric motor 7 which drives a lead screw 8, the latter being secured by way of a suitable link 9 to the lower end of the front of the carriage 4. It will be appreciated that, as shown in the drawing, the carriage 4 is at the right hand extremity of its slidable movement. If it is desired to move the bed 3 to the left, the motor 7 is actuated, thus extending the lead screw 8 and moving the carriage 4 to move to the left on its rollers 5 and the rails 6. The motor 7 is preferably a d.c. motor, because such motors can in general be stopped more abruptly than a.c. motors, and the motor 7 has, of course, to be a reversible motor.

In order that the position of the carriage 4 (and thus of the bed 3) relative to the frame 1 may be easily monitored, the components shown in FIGS. 2 and 3 are provided, some of these components being fixedly attached to the frame 1 and others being fixedly attached to the carriage 4; a suitable position for such components being indicated by the dashed rectangle marked 10, 18 in FIG. 1.

Referring now to FIGS. 2 and 3, in which components common to both FIGS. are identified by the same reference numbers in each, a scale 10, marked in centimetres and half centimetres, is secured to the frame 1. Also secured to the frame 1 are a cover plate 11 and a rack member 12 which has ridges such as 13 and notched such as 14 aligned respectively with the centimetre and half centimetre markings on the scale 10. The scale 10 and the rack 12, once aligned, are secured together, and the entire assembly thus provided is movable by means of a screw 15 for a reason which will become clear later.

Carried by the carriage 4 is an assembly comprising a bracket arrangement 16, 17 which supports a pointer 18 and a pair of micro-switches 19 and 20. The pointer 18 is arranged to protrude between the cover plate 11 and the scale 10 so as to overlie the scale and thereby indicate the relative positions of the carriage 4 and the frame 1. Each of the micro-switches carries, at the end of its toggle, a cam follower 21, 22. These cam followers are so spaced that, when one is on a ridge of the rack 12, the other is in the notch behind an adjacent ridge, and vice versa, so that when the pointer 18 overlies one of the full centimetre markings on scale 10 the switch 19 is closed and the switch 20 is open, and when the pointer 18 overlies one of the half centimetre markings the switch 19 is open and the switch 20 is closed. This arrangement is used to enable the apparatus to be accurately set up.

In operation, to install a patient in the apparatus, the motor 7 is actuated to move the carriage 4 to its fully leftwards position relative to the frame 1, and the bed 3 is pulled to its "fully out" position relative to the carriage 4. The patient is placed in the bed 3, and secured thereto by means of a plastic tape which is passed over his torso in the region of interest and secured beneath the bed. A convenient technique for securing the tape to the bed comprises the "Velcro" technique in which the tape is formed with many minute nylon hooks and the bottom of the bed 3 is formed with corresponding minute nylon eyes, so that the tape can be secured to the bed merely by applying pressure. Air gaps between the patient and the bed are usually minimised by the use of suitable packing material.

The bed 3 is then pushed to its "fully in" position relative to the carriage 4 and is locked thereto. The motor 7 is then actuated to cause the lead screw 8 to pull the carriage 4 to the right, thereby moving the patient's feet into and through the region indicated by the arrow 2 in FIG. 1. The frame 1 carries a suitable light source (not shown) which is caused to direct a fine line of light on to the patient's body at the position indicated by the arrow 2. By this means, the part of the patient's body which for the time being is in the plane of irradiation is illuminated by the fine line of light. The part of the patient's body which is to be examined is usually marked prior to the examination, and thus when the mark is illuminated by the fine line of light the motor 7 is de-actuated and the motion of the carriage 4 is stopped.

It will be appreciated that the carriage 4 may be stopped with the pointer 18 between two markings on the scale 10, and to facilitate subsequent operations the scale 10 (and the rack 12) is moved in the direction of motion of the carriage 4 relative to the pointer (and also relative to the frame 1) by means of the screw 15. The scale 10 and the rack 12 are mounted in suitable slides (not shown) to allow this movement to occur. Once the pointer is aligned with one of the markings on scale 10, one of the micro-switches 19 or 20 is opened and a 'hold' lamp on the apparatus, which indicates that a misalignment exists, is extinguished. Suitably the 'hold' lamp (not shown) is energised from a supply via series connected switches controlled in response to the condition of the switches 19, 20; these latter switches being arranged to open only when their respective cam followers are squarely in a notch of the rack 12.

The apparatus is now ready to scan the patient, the radiation source and the detector array being accurately aligned with the part of the patient's body to be examined. Once that particular section has been scanned, it may be desired to scan another section, parallel to the first, and spaced therefrom by (say) one centimetre. If this is the case, the motor 7 is actuated and caused to drive the lead screw 8 in the appropriate direction until the pointer 18 overlies another marking on scale 10 which lies one centimetre to either side of the marking which was indicated by the pointer when the first examination was made. The extinguishing of the 'hold' lamp indicates when a movement of exactly one centimetre has been carried out, the scale 10 being an aid to the operator however since the "hold" lamp is extinguished after every half centimetre of travel.

If desired, the movement of the carriage 4 can be automatically controlled step-wise as follows. The motor 7 is actuated to drive the carriage in a chosen direction. The drive continues until one of the micro-switches 19, 20 is opened (i.e. after one half centimetre of travel). If it is required to move the carriage 4 further, the motor 7 is actuated again. This step-wise operation is continued until the required amount of movement has taken place.

Preferably the apparatus has facility for continuous movement of carriage 4 as well as step-wise movement, and moreover, by controlling the operation of motor 7 in response to one of the micro-switches 19, 20 (rather than both of them) the stepped movement can be effected in one centimetre steps instead of half centimetre steps. Thus a given apparatus may have facility for continuous movement of carriage 4 relative to the frame 1, for installation of a patient and initial setting up, and for stepped movement of the carriage 4 in centimetres or half centimetres as controlled by a selector switch (not shown).

Should it be required to take a predetermined number of slices each at, say, 1cm spacings from the previous one, it is clearly possible to arrange for the apparatus to do this automatically.

What we claim is:

1. A driving and positioning arrangement for radiography, including a frame member having an apertured housing, a carriage supported by said frame member, the carriage being adapted to support a patient in a generally horizontal position and being movable in a direction longitudinal of the patient's body, and the aperture being such as to accommodate at least part of said body, drive means for moving said carriage, and with it the patient, in said longitudinal direction so as to dispose a predetermined slice of the patient's body in a position, within said housing, in which it can be irradiated with penetrating radiation, and a scale member having a first part, incorporating a scale formed with markings, and a second part, incorporating a pointer, one of said parts being suported by said frame member and the other of said parts being supported by said carriage so that said two parts are disposed in overlying relationship, with said pointer overlaying said scale to indicate the disposition of said carriage relative to said frame member, and means for moving at least one of said parts, in said longitudinal direction, relative to its respective supporting member, to cause said pointer and said scale to assume a predetermined relative position when said selected slice is in said position in which it can be irradiated, and wherein said first part also includes a rack member rigidly secured to said scale member and positioned so that the ridges and notches of said rack are disposed adjacent respective ones of said markings.

2. An arrangement according to claim 1 wherein said second part also includes first and second micro-switches having cam followers on the toggles thereof and wherein said cam followers are constrained to move along said rack and to ride over said ridges and notches, each switch being open circuited when its respective cam follower is disposed in a notch of said rack.

3. A radiographic system comprising:
   a frame member having a housing with an aperture dimensioned to permit passage therethrough of at least part of a patient's body;
   a carriage for supporting the patient's body in a generally horizontal position;

means for supporting the carriage and for moving the carriage, and with it the patient's body, relative to and through the aperture, generally along the longitudinal axis of the patient's body, to dispose a selected slice of the body at a selected position, relative to the aperture, for irradiation of said slice with penetrating radiation;

a scale member having a first part supported by said frame member and a second part supported by said carriage and moving therewith relative to said aperture, said parts of the scale member being juxtaposed and being dimensioned and marked to indicate, by their positions with respect to each other, the position of the carriage relative to the aperture;

means for selectively moving at least one of said scale member parts relative to the other, while the frame member and the carriage remain stationary, to cause said scale member parts to assume a selected juxtaposition relative to each other when said selected slice of the body is disposed at said selected position relative to the aperture of the frame member housing;

one of said scale member parts including a rack member with alternating ridges and notches extending along said longitudinal axis of the patient's body and the other one of said scale member parts including a first and a second microswitch each having a first and a second state;

means for placing each microswitch in its first or in its second state depending on whether a ridge or a notch of rack member is disposed at a selected position relative to the microswitch, the changes in state of said microswitches during relative movement of the two scale member parts being an indication of the extent and direction of such movement.

* * * * *